(12) United States Patent
Woehr

(10) Patent No.: US 6,709,419 B2
(45) Date of Patent: Mar. 23, 2004

(54) SHORT CATHETER

(75) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 38 days.

(21) Appl. No.: 09/727,747

(22) Filed: Dec. 1, 2000

(65) Prior Publication Data

US 2001/0018573 A1 Aug. 30, 2001

(30) Foreign Application Priority Data

Dec. 1, 1999 (DE) .................. 299 21 084 U

(51) Int. Cl.[7] ............................................ A61M 5/178
(52) U.S. Cl. ................................................. 604/164.07
(58) Field of Search ........................... 604/164.07, 164, 604/243, 181, 154

(56) References Cited

FOREIGN PATENT DOCUMENTS

WO    WO99/08742    *  2/1999

* cited by examiner

*Primary Examiner*—Henry Bennett
*Assistant Examiner*—Sabrina Dagostino
(74) *Attorney, Agent, or Firm*—Christie, Parker & Hale, LLP

(57) ABSTRACT

A catheter assembly is provided which provides a flexible catheter tube having one end provided with a catheter hub. A hollow needle having a needle hub on its end is installed in the catheter tube with its sharp end extending out from one end of the catheter tube and a portion of the needle extending through the catheter hub. A needle shield, which is on the needle within the interior of the catheter hub, is biased axially within the catheter hub with its ends being fixed to prevent axial expansion.

20 Claims, 2 Drawing Sheets

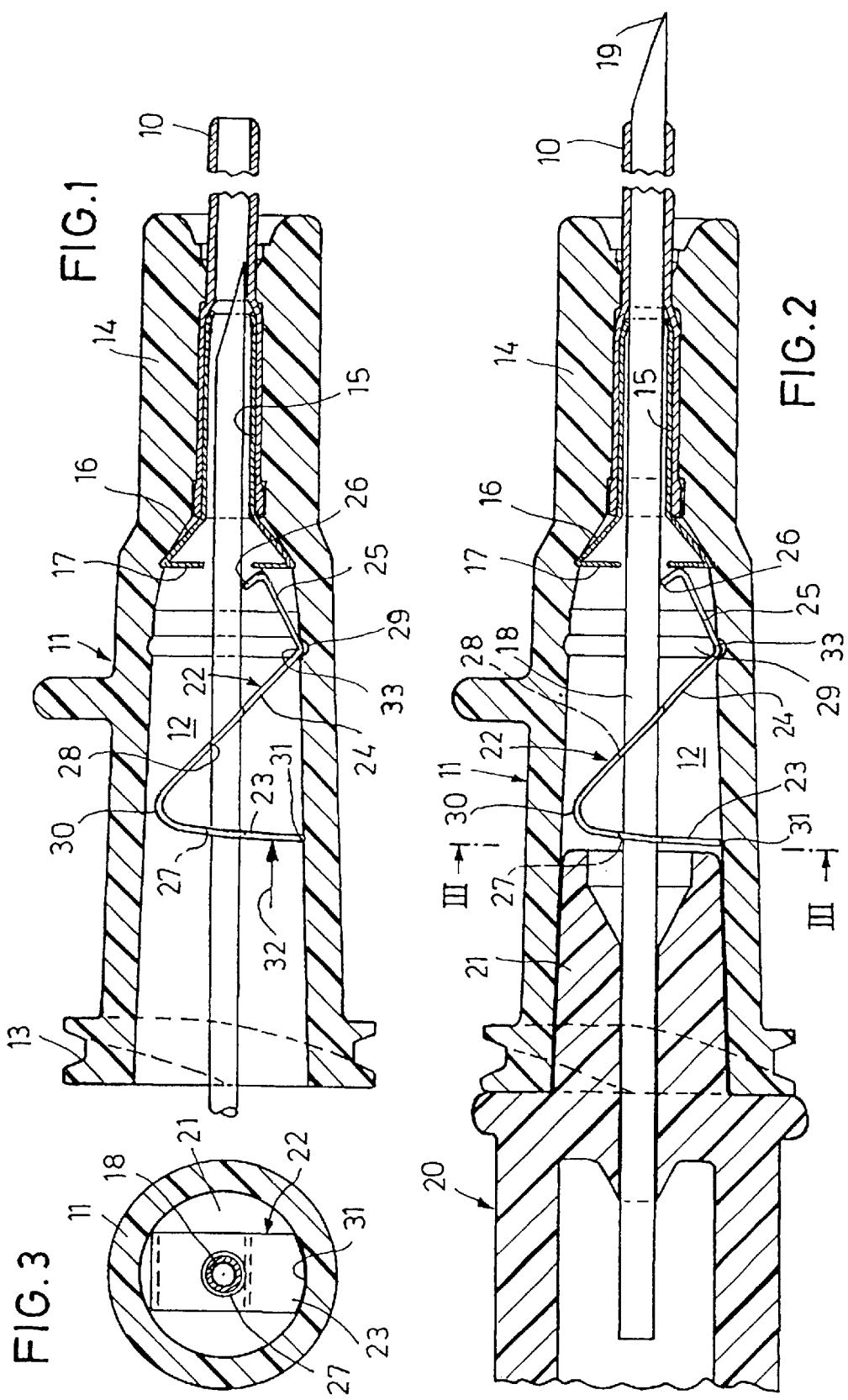

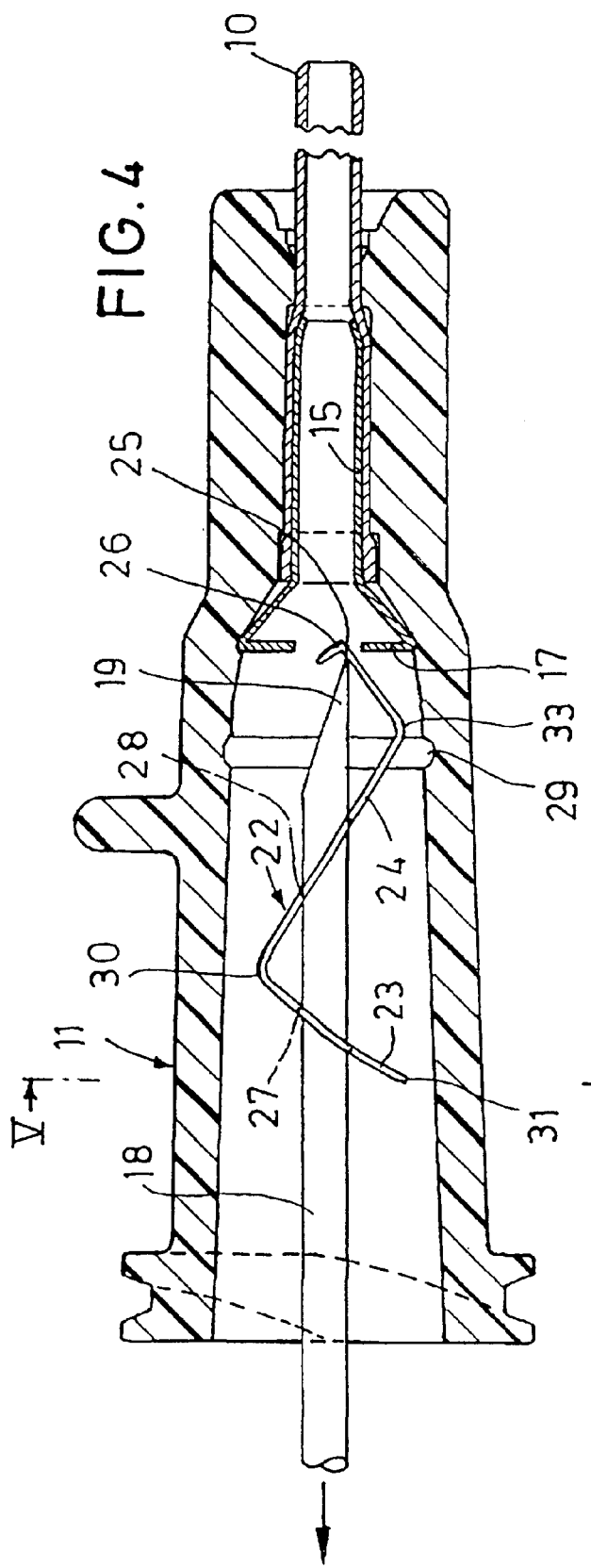
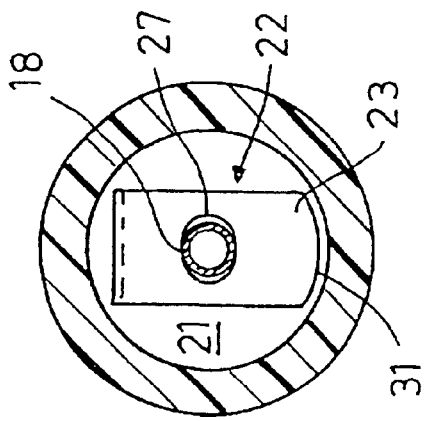

SHORT CATHETER

CROSS-REFERENCE TO RELATED APPLICATION

The present application relates to German Utility Model DE 29921084.7, filed Dec. 1, 1999.

The present invention refers to a short catheter in which the needle inserted into the catheter tube is made unserviceable by a needle shield after withdrawal.

Short catheters are also referred to as vein catheters or IV-catheters. They have a flexible catheter tube having one end provided with a catheter hub. A hollow needle is inserted into the catheter tube, the needle having a cutting needle tip at the distal end and a needle hub at the proximal end. By the needle tip, the needle and the surrounding catheter tube is inserted into the body of a patient. When the needle tip has entered a vein, the needle is withdrawn.

From WO 99/08742, a short catheter is known, wherein the needle is provided with a needle shield. The needle shield consists of a elastic metal clamp that is contained in the cavity of the catheter hub and as holes for the passage of the needle. A hook member of the needle shield presses the needle from the side. When, upon the withdrawal of the needle, the needle tip passes the hook member, the hook member snaps over the needle tip so that the hook member covers the needle tip which is no longer accessible. Thus, people are kept safe from being injured by the needle tip. In particular, the danger of contamination by germs clinging to the needle, transferred when the needle was used for the first time, is reduced. The needle shield guarantees that the needle can be used only once so that a contaminated needle cannot be used with another patient. To prevent the needle shield from slipping beyond the distal needle end, the needle may be provided with a corresponding locking means in the form of a notch or a not circular portion forming a distal stop for limiting the movement of the needle shield.

It is an object of the present invention to provide a short catheter comprising a needle shield wherein a clamping effect firmly holds the needle shield in the needle tip covering position.

The present short catheter has the features mentioned in claim 1. According to the invention, the needle shield is biased axially within the needle shield, its ends being fixed to prevent axial expansion In the biased state, the needle may easily be pushed through the holes in the needle shield since the holes are orientated such that the needle is easily displaced. In the activated state, i.e., when the needle tip has passed the hook member, the hook member snaps over the needle tip, thus releasing the axial bias of the spring element. The spring element is thereby returned to its stretched original shape. Thus, the holes that previously surrounded the needle with a slight gap suddenly become narrower in one direction, whereby the spring element firmly engages the needle. The release of the axial tension and the return of the spring element cause a tight clamping of the needle at the edges of the holes in the spring element. Therefore, in many cases, locking or blocking means at the needle can be omitted so that the needle must not be modified with respect to conventional needles.

To be able to accommodate the axially compressed needle shield in the interior of the catheter hub, the catheter hub must be provided with a holding means forming a stop for the distal end of the needle shield, i.e. the hook member. Preferably, such a holding means is a metal member protruding into the catheter tube and supporting the same in the catheter hub. Such a metal member is usually provided in a catheter hub as an internal catheter support. The metal member may be modified in a simple manner to form an abutment shoulder for the needle shield. This abutment shoulder may be an end wall that is formed to the opening end of a funnel of the metal member.

Preferably, a proximal holding means consists of an end edge of the needle shield that projects into the wall of the catheter hub. This end edge may be sharpened and penetrate into the wall of the catheter hub, when the needle shield is mounted.

The following is a detailed description of an embodiment of the invention with reference to the drawings, in which FIG. 1 is a longitudinal section through the short catheter, FIG. 2 is a longitudinal section after insertion of the needle into the short catheter being ready for use.

FIG. 3 is a sectional view along line III—III in FIG. 2,

FIG. 4 is a longitudinal section during withdrawal of the needle, and

FIG. 5 is a sectional view along line V—V of FIG. 4.

The short catheter illustrated comprises a flexible catheter tube 10 of elastic plastic material having its proximal end provided with a catheter hub 11. The catheter hub 11 consists of an elongate hollow plastic member with a slightly conical interior 12 and a Luer connector 13 at the proximal end. The distal end portion 14 is tubular. The catheter tube 10 extends therethrough up to the interior 12. A tubular metal member 15 is inserted into the proximal end of the catheter tube 10, which expands the catheter tube and presses it against the wall of the tubular portion 14. At the proximal opening end of the metal member 15, the metal member is flared in the manner of a funnel 16. The opening end of the funnel 16 is formed with an end wall 17 directed radially inward.

A hollow needle 18 is inserted into the catheter tube 10, having a cutting needle tip 19 at the distal end. The needle 18 is made of steel. At the rear end, it is connected to a needle hub 20 of plastic material. The needle hub 20 abuts the proximal end of the catheter hub 11 and a frustoconical projection 21 thereof, loosely fitting into the catheter hub 11, protrudes into the interior 12.

The interior 12 accommodates the needle shield 22 consisting of a spring member made of bent spring steel sheet. The needle shield is generally bent in a Z-shape, with a rear leg 23, a middle leg 24 and a front leg 25 being provided in succession. The front leg 25 has a hook member 26 formed thereto, angled off by more than 90°. The rear leg 23 and the middle leg 24 are each provided with a hole 27, 28.

As illustrated in FIG. 1, the needle shield 22 is inserted into the catheter hub 11 while sitting on the needle 18, the hook member 26 being set against the end wall 17 of the metal member 16. Then, using a tool (not illustrated) inserted into the interior 12 from the proximal end, an axial pressure is exerted in the direction of the arrow 32, the needle shield 22 being compressed in the axial direction. The axial direction follows the orientation of the axis of the catheter tube 10.

During the axial compression, a front bend 33 of the needle shield, formed between the sections 24 and 25, is pressed into an inner circumferential groove 29 of the interior. An opposite bend 30 connects the sections 23 and 24.

In this compressed state of the needle shield 22, the holes 27, 28 are circular in axial projection. This means that the hole 28 in the oblique middle leg 24 is oval and is larger in the longitudinal direction than in the transverse direction.

When the needle shield 22 is compressed axially, the end edge 31 of the section 23 is pressed into the wall of the catheter hub 11. Thus, the rear end of the needle shield penetrates into the wall, whereas the front end of the needle shield is supported on the end wall 17. In this state, the needle 18 may be inserted from the proximal end, passing through the holes 27 and 28 with a clearance and being advanced without any problems. The hook member 26 is displaced radially outward by the needle 18 so that, after further advancing the needle 18, it presses against the needle from the side.

FIGS. 4 and 5 illustrate he short catheter during the withdrawal of the needle 18 from the catheter tub 10 and the catheter hub 11. During the withdrawal of the needle 18, the hook member 26 that previously pressed against the needle from the side snaps over the needle tip 19. The previously axially compressed needle shield is relaxed and the end edge 31 comes clear of its engagement in the needle hub. The resilient needle shield 22 thus extends axially and the sharp edges of the holes 27, 28 firmly engage the needle 18. As can be seen in FIG. 5, the hole 27 becomes an ellipse, seen in axial projection. As soon as the needle shield has been activated by the needle tip 19 passing the hook member 26, the hook member 26 snaps over the needle tip and the needle shield firmly engages the needle. The hook member 26 now covers the needle tip and blocks any distal movement of the needle tip relative to the needle shield. The fact that the needle shield is axially expanded and separates from the catheter hub at its end edge 31 makes it freely movable within the catheter hub. After the needle shield is activated, its two holes 27, 28 engage a total of four points on the needle, as shown in FIG. 5. The needle 18 is a cylindrical round needle without any notches, projections or non-circular portions.

What is claimed is:

1. A short catheter comprising:
   a catheter tube with a catheter hub at its proximal end,
   a hollow needle passing through the catheter tube having a needle hub at the proximal end,
   the needle hub having a projection protruding into an interior of the catheter hub, and
   a needle shield arranged on the needle within the interior of the catheter hub, the needle shield being a spring member with holes for the passage of the needle and with a hook member at the distal end,
   wherein the needle shield is provided in an axially biased state within the catheter hub with its ends being fixed against axial expansion, and
   wherein at least one of the ends is fixed against axial expansion by pressing an end edge of one of the ends against an interior surface of the catheter hub.

2. The short catheter of claim 1, wherein a distal blocking member is a metal member protruding into the catheter tube and supporting the catheter tube in the catheter hub.

3. The short catheter of claim 2, wherein the metal member has an inward directed end wall at the opening end of a funnel.

4. The short catheter of one of claims 1–3, wherein a proximal blocking means is an end edge of the needle shield that projects into the wall of the catheter hub.

5. The short catheter of claim 1, wherein the hook member presses against the needle and, when the needle tip passes the hook member, snaps over the needle tip such that the needle shield relaxes and engages the needle from the side by the edges of the holes.

6. The short catheter of claim 1, characterized in that the holes are oval such that, with the needle shield axially compressed, the holes are round in axial projection and surround the needle with a clearance.

7. A short catheter assembly comprising:
   a catheter hub, wherein the catheter hub comprises an interior space and a catheter tube disposed thereon;
   a needle hub, wherein the needle hub comprises a needle passing through the interior space of the catheter hub and the catheter tube; and
   a needle shield, wherein the needle shield comprises a front leg and a rear leg, and
   wherein the needle shield is axially biased by abutting the front leg against an end wall and by wedging an end edge of the rear leg against a wall surface of the interior space of the catheter hub.

8. A needle assembly comprising:
   a needle hub having a projection extending into an interior cavity of a catheter hub;
   a needle, wherein the needle passes through the interior cavity and extends beyond the catheter hub; and
   a needle shield, wherein the needle shield comprises a front leg, a middle leg, a rear leg, an opening on each of the middle leg and rear leg; a first position, and a second position;
   wherein in the first position, the front and rear legs are fixed against axial expansion and the openings on the middle leg and the rear leg have substantially circular projections; and
   wherein in the second position, the needle moves proximal of the front leg and the front leg recoils to axially expand the needle shield.

9. The short catheter assembly of claim 7, further comprising a tubular metal member coaxially disposed with the needle.

10. The short catheter assembly of claim 9, wherein the end wall extends from a proximal end of the tubular metal member.

11. The short catheter assembly of claim 7, further comprising an inner circumferential groove in the interior space of the catheter hub.

12. The short catheter assembly of claim 11, further comprising a middle leg and wherein the middle leg and the front leg defines a front bend therebetween.

13. The short catheter assembly of claim 12, wherein the front bend is wedged in the circumferential groove.

14. The needle assembly of claim 8, further comprising a tubular metal member coaxially disposed with the needle.

15. The needle assembly of claim 8, wherein the front leg abuts against an end wall in the first position.

16. The needle assembly of claim 8, wherein an end edge of the rear leg is wedged against the interior cavity of the catheter hub.

17. The needle assembly of claim 14, further comprising an end wall extending from a proximal end of the tubular metal member.

18. The needle assembly of claim 17, wherein the front leg abuts against the end wall in the first position.

19. The needle assembly of claim 8, wherein the middle leg and the front leg defines a front bend therebetween.

20. The needle assembly of claim 19, further comprising a circumferential groove in interior cavity of the catheter hub, and wherein the front bend is wedged within the circumferential groove.

* * * * *

UNITED STATES PATENT AND TRADEMARK OFFICE
CERTIFICATE OF CORRECTION

PATENT NO. : 6,709,419 B2
DATED : March 23, 2002
INVENTOR(S) : Kevin Woehr

It is certified that error appears in the above-identified patent and that said Letters Patent is hereby corrected as shown below:

Column 1,
Line 45, after "expansion" insert a period (.)

Column 3,
Line 10, "he short catheter" should be -- the short catheter --

Column 4,
Lines 44 and 61, replace "definns" with -- define --
Line 63, after "in" and before "interior" insert -- the --

Signed and Sealed this

Seventh Day of September, 2004

JON W. DUDAS
*Director of the United States Patent and Trademark Office*